(12) United States Patent
Manquez Hatta et al.

(10) Patent No.: US 9,980,635 B2
(45) Date of Patent: May 29, 2018

(54) SYSTEM AND DEVICE FOR PRELIMINARY DIAGNOSIS OF OCULAR DISEASES

(71) Applicant: EYECARE S.A., Santiago (CL)

(72) Inventors: Maria Eliana Manquez Hatta, Santiago (CL); Humberto Lobos Sucarrat, Santiago (CL)

(73) Assignee: EYECARE S.A., Santiago (CL)

( * ) Notice: Subject to any disclaimer, the term of this patent is extended or adjusted under 35 U.S.C. 154(b) by 363 days.

(21) Appl. No.: 14/597,213

(22) Filed: Jan. 14, 2015

(65) Prior Publication Data

US 2015/0257639 A1  Sep. 17, 2015

(30) Foreign Application Priority Data

Mar. 12, 2014 (CL) ................................. 00594/2014

(51) Int. Cl.
| | | |
|---|---|---|
| G06K 9/00 | (2006.01) | |
| A61B 3/00 | (2006.01) | |
| A61B 3/14 | (2006.01) | |
| A61B 3/11 | (2006.01) | |

(52) U.S. Cl.
CPC ............ *A61B 3/0025* (2013.01); *A61B 3/112* (2013.01); *A61B 3/14* (2013.01)

(58) Field of Classification Search
None
See application file for complete search history.

(56) References Cited

U.S. PATENT DOCUMENTS 6,095,989 A * 8/2000 Hay ..................... A61B 3/0025
600/558
6,595,641 B1 * 7/2003 Braeuning ............. A61B 3/085
351/208
2005/0041121 A1 * 2/2005 Steinberg ........... G06K 9/00248
348/239
2013/0235346 A1 * 9/2013 Huang ................... A61B 3/152
351/208
2014/0015930 A1 * 1/2014 Sengupta ........... G06K 9/00771
348/46
2014/0079319 A1 * 3/2014 Lin ......................... G06T 5/007
382/167

FOREIGN PATENT DOCUMENTS

| EP | 2676441 A2 | 12/2013 |
|---|---|---|
| FR | 2 876 570 A1 | 4/2006 |
| WO | WO 99/66829 A1 | 12/1999 |
| WO | WO 2012/112901 A2 | 8/2012 |

OTHER PUBLICATIONS

Brückner, R., "Exakte Strabismusdiagnostik," *Ophthalmologica*, 144, pp. 184-198 (1962), with Machine translation.
Wheeler, M. C., "Objective Strabismometry in Young Children," *Trans Am Ophthalmol. Soc.*, 40, pp. 547-564 (1942).

* cited by examiner

*Primary Examiner* — Vikkram Bali
(74) *Attorney, Agent, or Firm* — Cooley LLP (57) ABSTRACT

A system for preliminary diagnosis of ocular diseases is proposed, in which from capturing a plurality of images of the eyes of a person, a final image, corrected by processing the images by a computer application, is obtained. The already mentioned application calculates the percentage of the colors composing the pupillary reflex of each eye, and compares the results with previous reference pictures obtained from normal cases and clinical cases of ocular diseases.

19 Claims, 6 Drawing Sheets

SYSTEM AND DEVICE FOR PRELIMINARY DIAGNOSIS OF OCULAR DISEASES

GOVERNMENT SUPPORT

This invention was made with U.S. Government support under Grant No. PGRD 16-0004-005 awarded by the United States Agency for International Development ("USAID"). The U.S. Government has certain rights in the invention.

BACKGROUND

1. Field of the Invention

The present invention relates to the field of ophthalmology, and particularly provides a system and a configured device for preliminary diagnosis of ocular diseases, which is based on imaging of the eyes and on the diagnosis of ocular disorders, on the basis of the processing of these images and the reflection values of the retina and/or the pupil that they provide.

2. Description of Related Art

An estimate based on the National Health Survey (ENS 2007) indicates that at least 1.5% to 2.6% of the Chilean population has some visual impairment, of this percentage is estimated that at least ¼ of them has chronic defects classified as blindness. The world situation is not so different, and this reveals that there are at least 12 million children under the age of 10, which is the age group of preventive control, suffer from visual impairment due to refractive error (myopia, strabismus or astigmatism) in addition there are more severe cases like ocular cancer that affects 1 in 12,000 live births, which is usually seen in children up to 5 years old. All of these conditions and others, in most cases can be corrected without major complications with a preventive diagnosis and effective treatment in infants from birth to about 5 years old, preventing these disorders getting worse with time and treatment being too expensive, ineffective or simply being too late to be implemented.

Most of these problems could be detected at an early age, but require continuous medical supervision and examinations which are carried out with high-cost instruments that also require the presence of specialists to use them.

For the group of infants (0-5 years) which is the control group and primary diagnosis, there are two key problems in performing these tests: it is difficult to make that infants focus their gaze intently to any device that performs the test and also the ophthalmologist or pediatrician has only fraction of a second to capture the image before the pupil shrinks in response to the bright flash light. These problems lead to pediatricians are unable to detect ocular problems early, and therefore cannot effectively take preventive measures before the problem getting worse.

The red pupillary reflex is fairly well understood by ophthalmologists and pediatric specialists worldwide, and has been used as a diagnostic instrument around the world since the 60s. Normally, the light reaches the retina and a portion of it is reflected off the pupil by the choroid or posterior uvea, which is a layer of small vessels and pigmented cells located near the retina. The reflected light, seen from a coaxial instrument to the optical plane of the eye, normally present a reddish color, due to the color of blood and pigments of the cells, so this color can vary from shiny reddish or yellowish in people with light pigmentation to a more grayish red or dark pigmentation in people with dark pigmentation. In 1962, Bruckner (Bruckner R. Exakte Strabismus diagnostic bei 1/2-3 jahrigen Kindern mit einem einfachen Verfahren, dem "Durchleuchtungstest." Ophthalmologica 1962; 144: 184-98) described abnormalities in the pupillary reflex as well as in quality, intensity, symmetry or presence of abnormal figures, therefore, pupilar red color test is also known as Bruckner test. Another similar test is the Hirschberg test, which uses the corneal reflex to detect misalignment of the eyes, which enables to diagnose some degree of strabismus (Wheeler, M. "Objective Strabismometry in Young Children." Trans Am Ophthalmol Soc 1942; 40: 547-564). In summary, these tests are used to detect misalignment of the eyes (strabismus), different sizes of the eyes (anisometropy), abnormal growths in the eye (tumors), opacity (cataract) and any abnormalities in the light refraction (myopia, hyperopia, astigmatism).

The evaluation of the pupillary and corneal reflexes is a medical procedure that can be performed with an ophthalmoscope, an instrument invented by Francis A. Welch and William Noah Allyn in 1915 and used since the last century. Today, his company Welch Allyn, has products that follow this line as Pan Optic™. There are also photographic screening type portable devices for the evaluation of pupilar red color as Plusoptix (Patent application No. WO9966829) or Spot™ Photoscreener (Patent Application No. EP2676441A2), but the cost ranges between USD 100 to 500, they weigh about 1 kg and also require experience in interpreting the observed images.

With regard to state of the art, concerning computer applications for the prompt diagnosis of ocular diseases, the application No. FR2876570 A1 by Mawas, presents a process to obtain a picture with a camera and remit it in negative to a specialist ophthalmologist via email, in order to detect strabismus (Hirschberg test); however, this lacks the processing of the image, the immediately preliminary diagnosis and its application to mobile devices. The patent application No. US2013235346 A1 by Huang, points to a smart device application to obtain a set of pictures, at two specified working distances, and four orientations to run of photorefraction tests, Bruckner and Hirschberg test, but requires masks that function like outlines on the screen, where the patient's face is fixed to obtain working distances, and there is no subsequent processing of images for a higher quality image.

The present invention is a practical and reliable solution for rapid diagnosis of ocular problems, which allows a preliminary examination only with the use of smart phones or tablet type devices, currently used by millions of people worldwide. The application can be run by parents, paramedics, pediatricians and ophthalmologists without the need for a more complex instrument or experience in the use of these, and effectively allows conducting a test to detect ocular problems. This application prototype was tested in 100 infants, from which 3 children with problems were detected, and which were referred to specialists who positively found ocular problems. The system allows to conduct a preliminary medical test regarding to the pupillary reflex (pupillary red color test or Bruckner test) and corneal reflex (Hirschberg test).

SUMMARY OF THE INVENTION

The present invention relates to a system for the preliminary diagnosis of ocular diseases, said system comprising:
- a device for capturing images or a camera;
- a device generating light or a flash;
- a screen for displaying the image;
- a memory for storing data
- a computational application stored in the memory that executes the process of capturing a plurality of images of the eyes of an individual, and a final corrected image obtained through the processing of said plurality of images, by performing a post-processing of the final image corrected by calculating the percentage of the colors that compose the pupillary reflex of each eye and comparing it with the values obtained for previous clinical cases;

and a processor functionally attached to the camera, the flash, the screen and the memory, such that runs the application.

In the system of the invention, the memory further includes images for the comparison of the final corrected image with previously diagnosed clinical cases, with ocular diseases.

The system can be implemented by using a computational device, a smart phone, or any device with connection to a camera, either an internal camera or a webcam and a system of a lighting device, of a built-in flash type.

The present invention also includes an "ex vivo" method for the preliminary diagnosis of ocular diseases, comprising the steps of:

focusing the image of the individual's eyes, using a camera and a screen of a computing device;

eliminating ambient lighting; in case a light is on in the room, the light is turned off, and if there is natural light, closing the windows or curtains to decrease it;

capturing a plurality of images of the individual's eyes with said camera, using the flash;

processing the plurality of images, by using a computational application in order to obtain a final corrected image of the individual's eyes;

displaying the said final corrected image on the screen and visually comparing it with clinical cases previously diagnosed with ocular diseases.

For the processing of the plurality of images, in order to obtain a final corrected image, the computational application includes the following steps:

i. making a first selection of images from the plurality of images;

ii. obtaining an approximation of the area of the individual's face in each image of the said first selection;

iii. aligning the mentioned first selection of images, from the edge detection by its spatial translation in each image of the said first selection;

iv. determining the area of the two eyes in each image of the said first selection;

v. obtaining a determined location of the center of the two eyes from each image of the said first selection;

vi. making a second selection of images, from said first selection, to select a single image of the individual's eyes with greater sharpness;

vii. processing that said single image to obtain a final corrected image with greater focus;

viii. cutting the eyes of the individual from that final corrected image, from the determined location of the centers and calculating the area of the two eyes; and ix. post-processing the final corrected image, to detect the percentage of the colors that compose the pupillary reflex.

The computational application makes the said first selection from the plurality of images obtained by the camera, discriminating on the luminance of the pixels and selecting in said first selection between 1 and 60 images, preferably, between the best 10 images.

The computational application obtains the approximation of the individual's face, detecting it in a first image captured from the said first selection, and then cutting the area of all the later images to the first image for further processing.

On the other hand, for aligning the said first selection of the plurality of images, the computational application finds the edges in the first image captured from said first selection, and searches these edges in the later images, to calculate the translation of these images with respect to said first image. Then, it calculates the location of the centers of the pupil of each eye for each image, removing outliers and averaging the position of said centers obtained to get the best determined location of the centers.

The computational application makes a second selection with respect to the sharpness of each image of said first selection, obtaining a value which is representative of the sharpness of each image and selecting the one image with greater sharpness, which is corrected in order to obtain the final corrected image with greater focus, using the area of each eye and the determined location of the centers.

Finally, the computational application performing a post-processing of the final corrected image, by calculating the percentage of the colors that compose the pupillary reflex of each eye, selecting the red, white, orange and yellow colors.

In this process, the following three cases are defined:

If the red color is in a range greater than 50% of the pixels that compose the area of the pupil, in any of the eyes of the final processed image, the image is considered most likely of a normal eye.

If the red color is in a range greater than 50% of the pixels that compose the area of the pupil, while the yellow and/or orange percentages correspond to a higher range of 10% of the pixels that compose the area of the in one of the eyes of the final processed image, the eye probably presents a type of refractive defect.

If the red color is in a range lower than 50% of the pixels that compose the area of the iris and the pupil, while white corresponds to a percentage higher than 40% in any of the eyes of the final processed image the diagnosis corresponds to a suspicion for organic and/or structural disease.

Clinical cases that are previously diagnosed and used as reference for comparison of the images that the system of invention produce, consist of a set of three or more images previously obtained by the computing device, which represent normal cases, clinical cases of refractive defects and other ocular diseases.

Within the cases of refractive defects of the group that can be diagnosed with the system of the invention, we can found hyperopia, astigmatism and myopia; and it is also possible to make a fast screening of other ocular diseases, such as organic diseases and ocular functional diseases, Including tumors, malformations, strabismus, cataracts, etc.

DESCRIPTION OF THE DRAWINGS

The novel features believed characteristic of the application are set forth in the appended claims. However, the application itself, as well as a preferred mode of use, and further objectives and advantages thereof, will best be understood by reference to the following detailed description when read in conjunction with the accompanying drawings, wherein:

While the system and method of the present application is susceptible to various modifications and alternative forms, specific embodiments thereof have been shown by way of example in the drawings and are herein described in detail. It should be understood, however, that the description herein of specific embodiments is not intended to limit the application to the particular embodiment disclosed, but on the contrary, the intention is to cover all modifications, equivalents, and alternatives falling within the spirit and scope of the process of the present application as defined by the appended claims.

DETAILED DESCRIPTION OF THE PREFERRED EMBODIMENT

Illustrative embodiments of the preferred embodiment are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms to describe a spatial relationship between various components or to describe the spatial orientation of aspects of such components should be understood to describe a relative relationship between the components or a spatial orientation of aspects of such components, respectively, as the device described herein may be oriented in any desired direction.

The present invention relates essentially to a system and method employing a computational application that can be executed on mobile devices and related devices, which allows obtaining a preliminary examination of ocular conditions, using the pupillary and corneal reflexes obtained from a photograph of the eyes.

Unlike the old cameras of the non-digital age, digital cameras and mobile devices, like current smartphones or tablets, are programmed with a temporary setup between camera and flash, in such a way to avoid the reflection of the red pupil in the pictures that are obtained with them. However, is not well known that this reflex has important information about ocular diseases, and can be used for their detection as a preliminary screening using the invention.

Since mobile devices are currently used by millions of people around the world, the purpose of the present invention is to provide an application easy to use to the general population, without requiring the utilization of complex ophthalmic instruments, and which recreates the effect of old cameras that can capture the reddish reflex of the eyes, but also includes a processing of the obtained image, so this reflection to be sharper and more focused.

The present invention, therefore, is a useful tool for the early and preliminary detection of ocular diseases, which are then confirmed by specialists. Furthermore, this computational application has been particularly useful for avoiding problems associated to perform ocular examinations in infants, since through it is not necessary to sleep them, keep them focused, or subjected to long ocular examinations, is not necessary to dilate their pupils by using pharmacological drops, with the consequent disadvantages that they usually produce. The present invention can perform this examination by simply lowering the ambient lighting before taking the pictures of the eye, using the flash. Infants are the group of greatest need for continuous ocular controls, because at this age they can develop many of the ocular problems that could have on their lives as adults, which often fail to be detected early.

Figure 1:
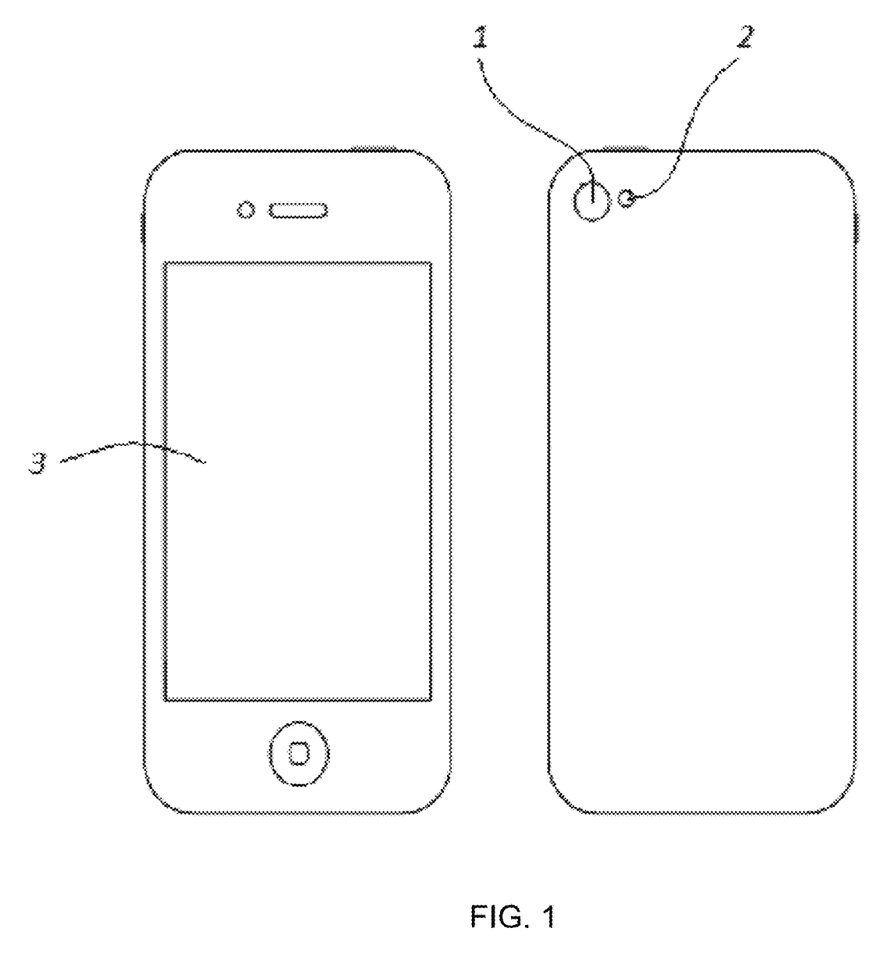
FIG. 1 is a front and rear view of a smart phone, according to the invention.

The computational application of the present invention can be installed in any electronic device. A non-limiting example of a smartphone, according to the invention, is an iPhone 4S®, marketed by Apple Inc., and shown in FIG. 1. This smartphone has a camera for capturing images (lens 1), a device generating light or flash 2, a screen 3 that allows displaying images and serves to focus on the individual, a memory that stores the application and images, and a processor that runs the application to obtain the final images.

Figure 2:
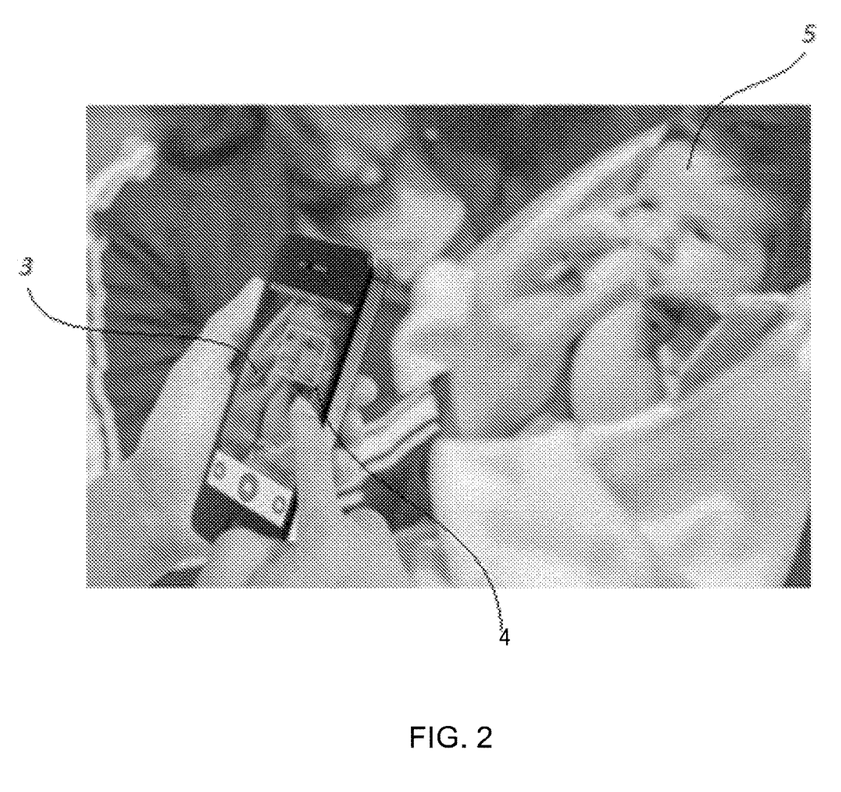
FIG. 2 is an example of using the device while the individual's eyes are focused, in this case, infant eyes.

In FIG. 2, is represented how the camera of the device in question is activated, the output of the camera is shown on screen 3. The focus point 4 is marked with respect to the individual's eyes 5 by touching the screen 3, in order to proceed, subsequently, to lower the amount of ambient lighting. The pupil dilates naturally being in low light, so, at this moment, the taking of a plurality of images is activated, using the application.

Figure 3:
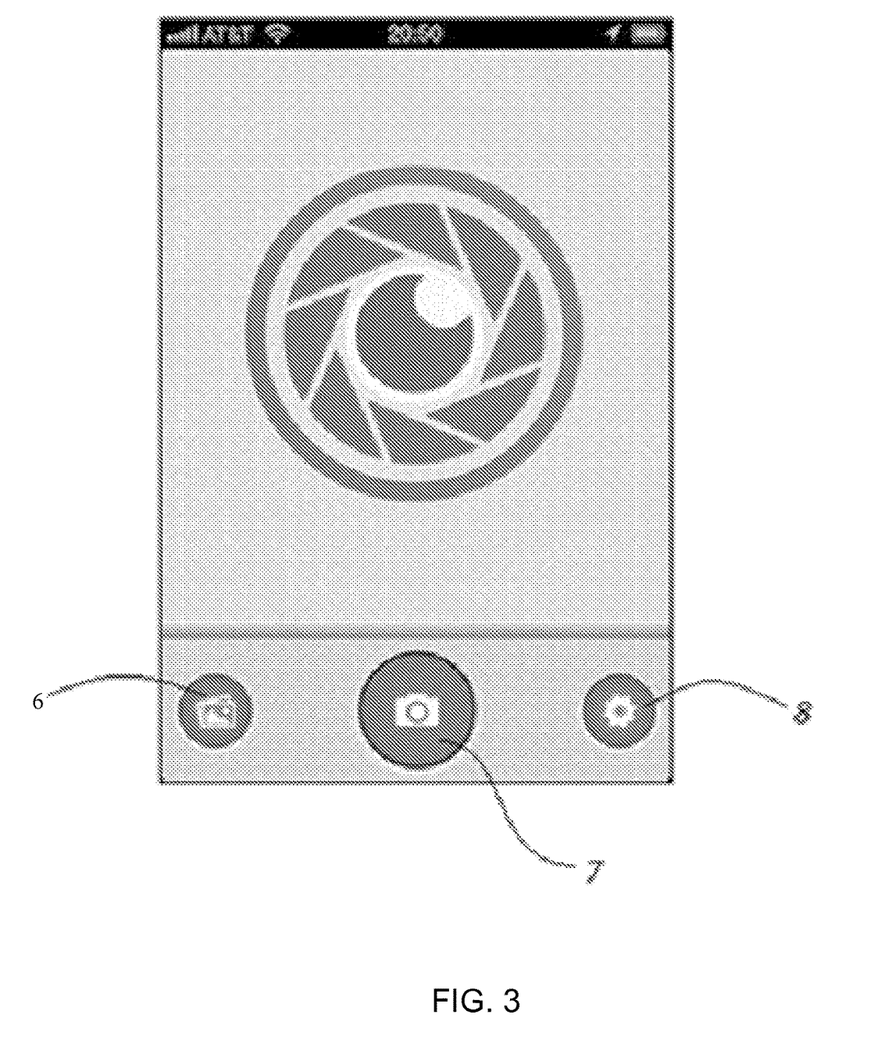
FIG. 3 is a screenshot of the application, running on a device according to the invention.

FIG. 3, which is a graphical representation of a screenshot of the application, shows the button 6 for the initiation of taking a plurality of images, a setting button 7 and a button 8 to display the images obtained.

To begin capturing pictures, the application turns on the flash light 2, but the pictures will begin to be processed when the application estimates that what is being captured is already under the influence of light from the flash. The application estimates the amount of light contained in each image, transforming these to Y'UV color space, which represent a luminance component Y' and two chrominance components UV. The application calculates the average of the component Y', which represents the luminance of the pixel. Then, calculating the luminance before starting and during the frames, the application discriminates from which frame to start capturing, as it is known from this frame, that the flash 2 is affecting the captured image.

Frames containing no flash light 2 are discarded. The application performs it by removing an arbitrary number of frames captured since the flash 2 started to work, so then be able to capture ten images to be used in the process.

The capture of the first image of the process is different from the others, since in this frame the approximate area of the individual's face is detected using an appropriate "haar cascade", which is a process that captures the best section of the individual's face, and this section is cropped, obtaining the image to be used; this minimizes the amount of information to be processed by the application. In order to obtain the rest of the images, the same detected area is cropped, obtaining images of the same size as the first. Notably, the first frames pictures since the flash 2 has an effect, where the greatest effect on the retina reflex occurs, because at that time the pupil is dilated by the little pre-flash light. For this reason, the number of used frames does not exceed ten.

By completing the capture of the ten images, a camera stabilization process is performed, which helps to reduce camera shake or movement of the person in the sequence. To achieve this, first the position of the prominent edges of the image ("good features to track") is detected. These same points are then searched in the next image frame by calculating the "optical flow". After obtaining the points of the first image in the following one, the calculation of the translational suffered by the following image, regarding its predecessor, is performed. For this, the average of the motion vectors of all the prominent edges of this is calculated by transferring the image by that amount. This allows the eyes to be always in the same position in all the taken pictures, so it is possible, as will be explained later, to perform the detection of the important features, using not one, but several pictures.

With the images already aligned the area enclosed by each eye of each of the images is calculated, using a "cascade haar" both for the right eye and the left eye. Afterwards, using the image gradients the center of the pupil of each eye is obtained in each image. After, the images where all the features could not be detected are discarded.

At this time, a set of positions of centers and a set of areas where the eyes are, are available. With this, it is possible to calculate a position that represents better the eye center. To do this, first all outliers from the set of centers are eliminated and then position of all of them are averaged. A similar process is applied to each of the squares enclosing the eyes, getting the best square enclosing each eye. At the end, the process selects the picture that is less blurry as the final image.

To perform the above, a defocusing of each of the images, using a Gaussian filter is performed. Then, the fast Fourier transform (FFT) is calculated, and the average of 90% of the highest values are calculated, obtaining a value that estimates how sharper the image is. The chosen image is also passed by another process called "unsharp masking" to focus it digitally, which consists of blurring the image, using a Gaussian blur and subtracting the result to the original image on a weighted basis for a larger focus. Then, the portion of the image is cropped in the best frame obtained in the previous step for each eye, and another image, corresponding to the pupil and iris of the eye is cropped, from the best center also obtained in the previous step.

By the process just described, a good reflection on the retina can be obtained, producing a color which allows diagnostic analysis. This color is usually related to the internal condition of the eye. In a normal patient, this will be reddish tonality; and in abnormal cases could detect a white color that may indicate the existence of some abnormal body into the eye, or a yellow color indicating some eye deformation. So a post processing in which it is necessary to detect what color appeared in the pupil reflex shooting takes place. To do this the amount of red, white and yellow color in the image of the pupil is calculated. To do this the image of the pupil of each eye is transformed to HSV color space and passed through a mask that leaves in color white all colors within a specific range. The percentage of white pixels is then calculated, getting the percentage of that color in the image.

Figure 4:
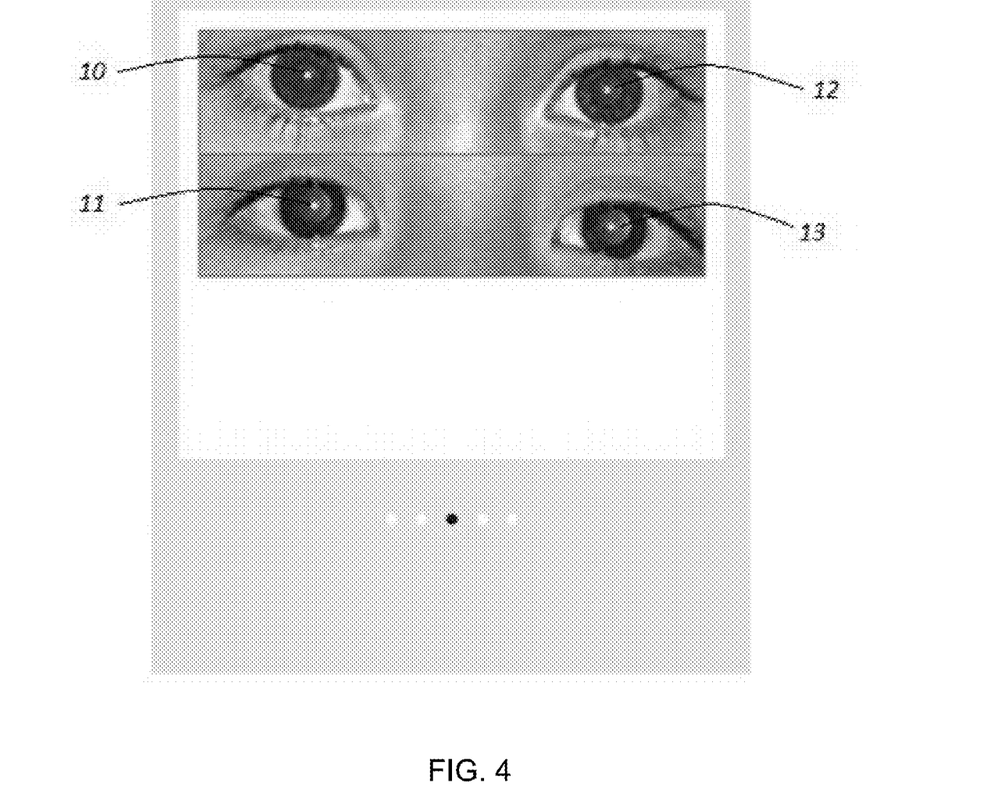
FIG. 4 is an example of a diagnosis type, obtained from the device, according to the invention, of the normal pupillary reflex.

If the predominant color is red, it is likely that the eye looks normal. FIG. 4 is an example of this case, where the reflection of the red pupil 10, 11, 12 and 13 seen in both eyes is normal.

Figure 5:
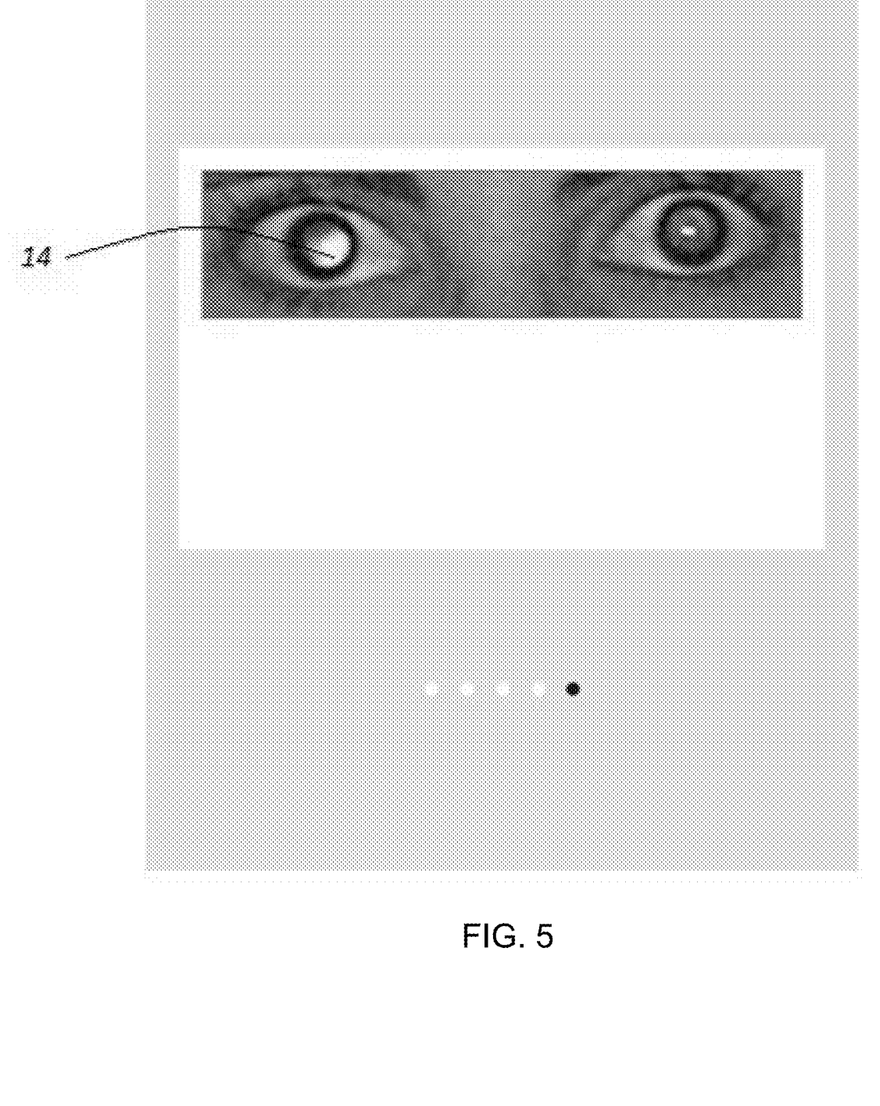
FIG. 5 is an example of a diagnosis type, of a pupillary reflex with refractive ocular problems.

If the predominant color is red, with a percentage of orange or yellow color, is likely to have a common problem in sight. FIG. 5 is an example of this case, where the presence of a yellow reflection in the right eye 14 of the patient may be a sign of refractive errors or strabismus. It is recommended for this patient to request a visit to the ophthalmologist.

Figure 6:
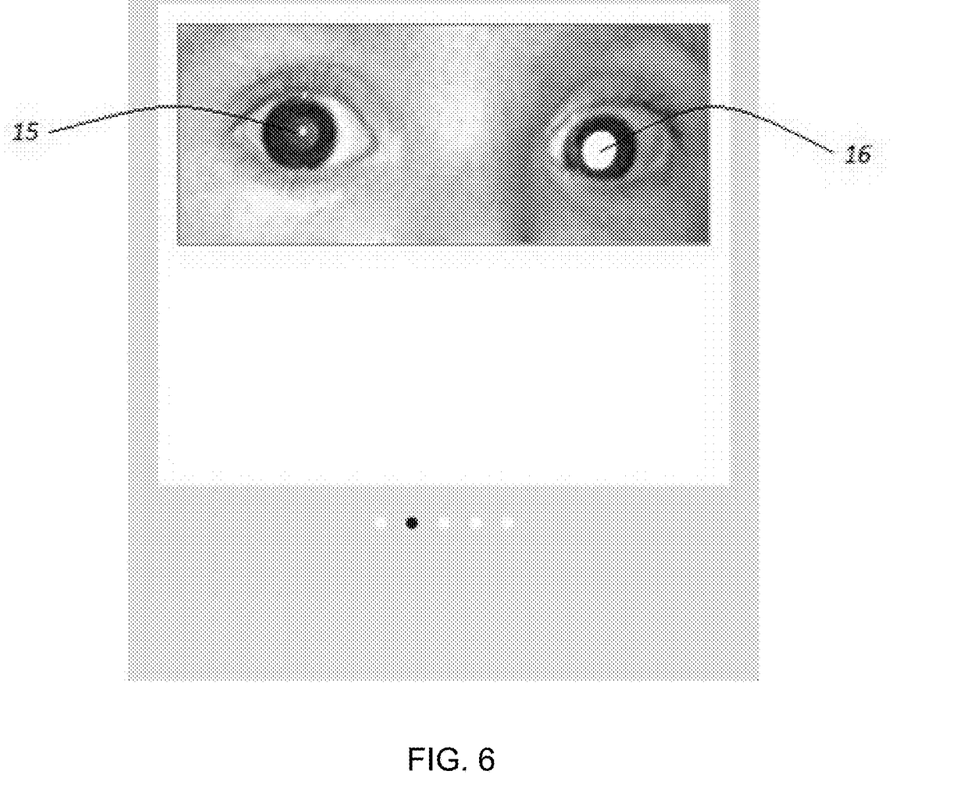
FIG. 6 is an example of a diagnosis type, of a pupillary reflex with serious ocular problems.

If the predominant color is white, there is probably a problem with a tumor disease in the eye. FIG. 6 is an example of this case, where the reflection of the red reflex seen in the right eye 15 is normal. The white reflection in the left eye 16 may be a sign of a dangerous condition within the patient's eye. It is recommended for the patient to visit an ophthalmologist as soon as possible, urgently.

In case none of the above situations occurs, the analysis does not reach a conclusive result, so the patient should require an expert and conduct more complex tests with the proper equipment, to obtain a more accurate diagnosis.

Figure 7A:
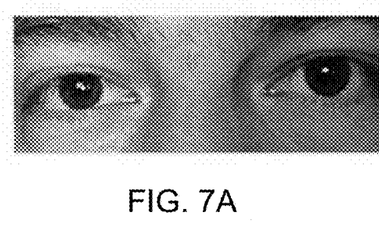
FIGS. 7A and 7B are a comparison of an image obtained by an electronic device according to the invention (FIG. 7A), compared to the final image processed by the application in the same computing device (FIG. 7B).
Figure 7B:
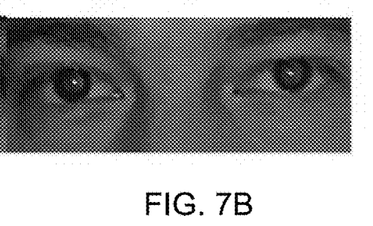

Finally, the final processed image (FIG. 7B) can be seen, to be used for diagnosing ocular diseases. FIGS. 7A and 7B show a comparison between a normally captured image with an electronic device, according to the invention (FIG. 7A) and the final image processed by the computer application (FIG. 7B).

The particular embodiments and steps disclosed above are illustrative only, as the application may be modified and practiced in different but equivalent manners apparent to those skilled in the art having the benefit of the teachings herein. It is therefore evident that the particular embodiments and steps disclosed above may be altered or modified, and all such variations are considered within the scope and spirit of the application. Accordingly, the protection sought herein is as set forth in the description. It is apparent that an application with significant advantages has been described and illustrated. Although the present application is shown in a limited number of forms, it is not limited to just these forms, but is amenable to various changes and modifications without departing from the spirit thereof.

What is claimed is:

1. A system for the preliminary diagnosis of ocular diseases, the system comprising:
   a camera;
   a flash;
   a screen for displaying at least one image;
   a memory for storing data and a computational application; and
   a processor coupled to the camera, the flash, the screen and the memory, wherein upon execution of the computational application by the processor, the processor:
      controls the camera and the flash to capture a plurality of images of the eyes of an individual, wherein the plurality of images have a same orientation; and
      processes said plurality of images to obtain a final corrected image by:
         estimating an amount of light contained in each image of the plurality of images;
         discarding one or more respective images that contain no flash light, based on the estimated amount of light contained in each image of the plurality of images, thereby obtaining a plurality of remaining images;
detecting, in a first image of the plurality of remaining images, an approximate area of the face of the individual using an appropriate haar cascade;
cropping said approximate area from said plurality of remaining images, thereby obtaining a plurality of cropped images;
performing a camera stabilization process on said plurality of cropped images, thereby obtaining a plurality of stabilized cropped images;
obtaining an average position of the center of the pupil of each eye of the individual and an average area enclosing each eye of the individual from said plurality of stabilized cropped images; and
selecting one stabilized cropped image of the plurality of stabilized cropped images that has the greatest sharpness as the final corrected image.

2. The system of claim 1, wherein:
the memory further stores images of previously diagnosed clinical cases with ocular diseases; and
upon execution of the computational application by the processor, the processor:
calculates, in the final corrected image, percentages of respective colors that compose the pupillary reflex of each eye; and
compares the calculated percentages of the respective colors with values obtained from the images of previously diagnosed clinical cases.

3. The system of claim 1, wherein the system comprises a smart phone that includes the camera.

4. The system of claim 3, wherein the smart phone further includes the flash.

5. A method for the preliminary diagnosis of ocular diseases, the method comprising:
capturing a plurality of images of the eyes of an individual with a camera using a flash, wherein the plurality of images have a same orientation;
processing the plurality of images, to obtain a final corrected image of the eyes of the individual; and
displaying said final corrected image on a display screen;
wherein processing the plurality of images comprises:
estimating an amount of light contained in each image of the plurality of images;
discarding one or more respective images that contain no flash light, based on the estimated amount of light contained in each image of the plurality of images, thereby obtaining a plurality of remaining images;
detecting, in a first image of the plurality of remaining images, an approximate area of the face of the individual using an appropriate haar cascade;
cropping said approximate area from said plurality of remaining images, thereby obtaining a plurality of cropped images;
performing a camera stabilization process on said plurality of cropped images thereby obtaining a plurality of stabilized cropped images;
obtaining an average position of the center of the pupil of each eye of the individual and an average area enclosing each eye of the individual from said plurality of stabilized cropped images; and
selecting one stabilized cropped image of the plurality of stabilized cropped images that has the greatest sharpness as the final corrected image.

6. The method of claim 5, wherein:
performing the camera stabilization process on said plurality of cropped images comprises aligning the plurality of cropped images by edge detection and spatial translation to obtain the plurality of stabilized cropped images; and
obtaining an average position of the center of the pupil of each eye of the individual and an average area enclosing each eye of the individual from said plurality of stabilized cropped images comprises:
determining respective areas enclosing the eyes of the individual in each image of said plurality of stabilized cropped images; and
obtaining respective locations of the centers of the eyes from each image of said plurality of stabilized cropped images.

7. The method of claim 6, wherein aligning the plurality of cropped images by edge detection and spatial translation to obtain the plurality of stabilized cropped images comprises:
detecting first edges in a first image of the plurality of cropped images;
detecting the first edges in at least one subsequent image of the plurality of cropped images; and
calculating a translation of the at least one subsequent image based on the detected first edges in the at least one subsequent image.

8. The method of claim 5, wherein:
estimating an amount of light contained in each image of the plurality of images comprises calculating a luminance of pixels in each image; and
discarding one or more respective images that contain no flash light comprises discarding the one or more respective images based on the calculated luminance.

9. The method of claim 5, wherein a number of said plurality of remaining images ranges from 10 to 60 images.

10. The method of claim 5, wherein obtaining said average position of the center of the pupil of each eye of the individual comprises:
calculating the location, in each image of the plurality of stabilized cropped images, of the center of the pupil of each eye to obtain a plurality of positions of the center of the pupil of each eye;
removing outliers from the plurality of positions to obtain a plurality of remaining positions; and
averaging the plurality of remaining positions to get the average position of the center of the pupil of each eye.

11. The method of claim 5, wherein selecting one stabilized cropped image of the plurality of stabilized cropped images that has the greatest sharpness as the final corrected image comprises:
defocusing each image of the plurality of stabilized cropped images using a Gaussian filter;
calculating a Fast Fourier Transform (FFT) for each defocused image to obtain an image sharpness value that estimates an image sharpness of each image; and
selecting the final corrected image based at least in part on respective image sharpness values.

12. The method of claim 5, further comprising:
calculating, from the final corrected image, percentages of respective colors in the pupillary reflex of each eye, wherein the respective colors include red, white, orange and yellow colors.

13. The method of claim 12, further comprising:
determining whether or not the red color is in a range greater than 50% of pixels that compose an area of the pupil of each eye in the final processed image.

14. The method of claim 13, wherein the red color is in a range greater than 50% of the pixels that compose the area of the pupil, and the method further comprises:
  determining whether or not the yellow color and/or the orange color correspond to percentages in a range greater than 10% of the pixels that compose the area of the pupil of each eye in the final processed image.

15. The method of claim 13, wherein the red color is in a range less than 50% of the pixels that compose the area of the iris and the pupil, and the method further comprises:
  determining whether or not the white color corresponds to a percentage greater than 40% of the pixels that compose the area of the pupil of each eye in the final processed image.

16. The method of claim 5, further comprising:
  comparing the final processed image with a plurality of previous images corresponding to previously diagnosed clinical cases,
  wherein the previously diagnosed clinical cases represent at least one of normal cases, clinical cases of refractive defects, and cases of other ocular diseases; and
  wherein said refractive defects are selected from the group consisting of hyperopia, astigmatism and myopia.

17. The method of claim 16, wherein said other ocular diseases are selected from the group consisting of organic diseases and functional diseases.

18. The method of claim 5, further comprising:
  processing said final corrected image to obtain a final corrected image with greater focus;
  cutting the eyes of the individual from the final corrected image with greater focus, from the average position of the center of the pupil of each eye and said average area enclosing each eye of the individual; and
  post-processing the final corrected image with greater focus, to determine percentages of respective colors that compose the pupillary reflex of each eye in the final corrected image with greater focus.

19. A method for the preliminary diagnosis of ocular diseases, the method comprising:
  capturing a plurality of images of the eyes of an individual with a camera using a flash;
  processing the plurality of images to obtain a final corrected image of the eyes of the individual; and
  displaying said final corrected image on a display screen,
  wherein processing the plurality of images comprises:
    estimating an amount of light contained in each image of the plurality of images;
    discarding one or more respective images of the plurality of images that contain no flash light, based on the estimated amount of light contained in each image of the plurality of images, thereby obtaining a plurality of remaining images;
    detecting, in a first image of the plurality of remaining images, an approximate area of the face of the individual using an appropriate haar cascade;
    cropping said approximate area from said plurality of remaining images, thereby obtaining a plurality of cropped images;
    performing a camera stabilization process on said plurality of cropped images, thereby obtaining a plurality of stabilized cropped images;
    obtaining an average position of the center of the pupil of each eye of the individual and an average area enclosing each eye of the individual from said plurality of stabilized cropped images; and
    selecting one stabilized cropped image of the plurality of stabilized cropped images that has the greatest sharpness as the final corrected image,
  wherein:
  estimating an amount of light contained in each image of the plurality of images comprises calculating a luminance of pixels in each image;
  discarding one or more respective images that contain no flash light comprises discarding the one or more respective images based on the calculated luminance;
  a number of said plurality of remaining images ranges from 10 to 60 images; and
  the method further comprises calculating, from the final corrected image, percentages of respective colors in the pupillary reflex of each eye, wherein the respective colors include red, white, orange and yellow colors.

* * * * *

UNITED STATES PATENT AND TRADEMARK OFFICE
CERTIFICATE OF CORRECTION

PATENT NO. : 9,980,635 B2  
APPLICATION NO. : 14/597213  
DATED : May 29, 2018  
INVENTOR(S) : Manquez Hatta et al.

It is certified that error appears in the above-identified patent and that said Letters Patent is hereby corrected as shown below:

Column 9
- In Claim 5, Line 59, replace "images thereby" with – images, thereby –
- In Claim 5, Line 62, replace "each eve" with – each eye –

Signed and Sealed this
Seventh Day of May, 2019

Andrei Iancu
*Director of the United States Patent and Trademark Office*